United States Patent
Quach et al.

(10) Patent No.: US 11,963,705 B2
(45) Date of Patent: *Apr. 23, 2024

(54) SYSTEMS AND METHODS FOR DISTRACTION

(71) Applicant: NuVasive Specialized Orthopedics, Inc., San Diego, CA (US)

(72) Inventors: Ricky Trieu Quach, Irvine, CA (US); Arvin Chang, Yorba Linda, CA (US); Alan J. Arena, Chino, CA (US); Adam G. Beckett, Mission Viejo, CA (US); Mark T. Dahl, South Afton, MN (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 325 days.

This patent is subject to a terminal disclaimer.

(21) Appl. No.: 17/239,565

(22) Filed: Apr. 24, 2021

(65) Prior Publication Data

US 2021/0251675 A1    Aug. 19, 2021

Related U.S. Application Data

(63) Continuation of application No. 16/298,339, filed on Mar. 11, 2019, now Pat. No. 11,439,449, which is a
(Continued)

(51) Int. Cl.
*A61B 17/88*    (2006.01)
*A61B 17/70*    (2006.01)
(Continued)

(52) U.S. Cl.
CPC ...... *A61B 17/8866* (2013.01); *A61B 17/7004* (2013.01); *A61B 17/7014* (2013.01);
(Continued)

(58) Field of Classification Search
CPC ..... A61B 17/88; A61B 17/8866; A61B 17/70; A61B 17/7014; A61B 17/7004;
(Continued)

(56) References Cited

U.S. PATENT DOCUMENTS

| 2,391,537 A | 9/1943 | Anderson |
| 2,702,031 A | 2/1955 | Wenger |

(Continued)

FOREIGN PATENT DOCUMENTS

| CN | 1697630 A | 11/2005 |
| CN | 101040807 A | 9/2007 |

(Continued)

OTHER PUBLICATIONS

Machine Translation of Japanese Application No. JP1991000722U, published Jul. 1, 1991, 6 pages.
(Continued)

*Primary Examiner* — Christopher J Beccia

(57) ABSTRACT

A system for moving a portion of a patient's body including a housing having a first cavity extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

20 Claims, 11 Drawing Sheets

Related U.S. Application Data continuation of application No. 14/981,762, filed on Dec. 28, 2015, now Pat. No. 10,271,885.

(60) Provisional application No. 62/097,005, filed on Dec. 26, 2014.

(51) Int. Cl.

| | | |
|---|---|---|
| *A61B 17/72* | (2006.01) | |
| *A61B 50/20* | (2016.01) | |
| *A61B 50/30* | (2016.01) | |
| *A61B 50/33* | (2016.01) | |
| *A61B 50/34* | (2016.01) | |
| *A61B 17/56* | (2006.01) | |
| *A61B 17/68* | (2006.01) | |

(52) U.S. Cl.
CPC ...... *A61B 17/7016* (2013.01); *A61B 17/7017* (2013.01); *A61B 17/7216* (2013.01); *A61B 50/20* (2016.02); *A61B 50/30* (2016.02); *A61B 50/33* (2016.02); *A61B 50/34* (2016.02); *A61B 2017/564* (2013.01); *A61B 2017/681* (2013.01)

(58) Field of Classification Search
CPC . A61B 17/7016; A61B 17/7017; A61B 17/72; A61B 17/7216; A61B 50/20; A61B 50/30; A61B 50/33; A61B 50/34
See application file for complete search history.

(56) References Cited

U.S. PATENT DOCUMENTS

| | | |
|---|---|---|
| 3,111,945 A | 11/1963 | Von Solbrig |
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,203,548 B1 | 3/2001 | Helland |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |

(56) References Cited

U.S. PATENT DOCUMENTS

| | | |
|---|---|---|
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 * | 5/2004 | Butsch ............... A61B 17/7216 606/57 |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 * | 7/2010 | Eksler ............... A61B 17/7016 606/86 R |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |

(56) References Cited

U.S. PATENT DOCUMENTS

| | | |
|---|---|---|
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,693,813 B2 | 7/2017 | Walker et al. |
| 10,271,885 B2 * | 4/2019 | Quach ............... A61B 17/7016 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |

(56) References Cited

U.S. PATENT DOCUMENTS

| | | |
|---|---|---|
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0209265 A1 | 8/2012 | Pool |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0031870 A1 | 1/2014 | Chang et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0324047 A1 | 10/2014 | Zahrly et al. |
| 2014/0350602 A1 | 11/2014 | Seme et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | 1991000722 U | 7/1991 |
| JP | H0956736 | 3/1997 |
| JP | 2002500063 A | 1/2002 |
| JP | 2011502003 A | 1/2011 |
| SU | 1197658 A1 | 12/1985 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |

OTHER PUBLICATIONS

Abe et al., "Experimental external fixation combined with percutaneous discectomy in the management of scoliosis.", SPINE, 1999, pp. 646-653, 24, No. 7.

Ahlbom et al., "Guidelines for limiting exposure to time-varying electric, magnetic, and electromagnetic fields (up to 300 GHZ). International Commission on Non-Ionizing Radiation Protection. ", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

(56) References Cited

OTHER PUBLICATIONS

Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", dated 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. SI05-SII5, No. 355S.
Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.

(56) References Cited

OTHER PUBLICATIONS

Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering•General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.

(56) References Cited

OTHER PUBLICATIONS

Zheng et al., "Force and torque characteristics for magnetically driven blood pump.", Journal of Magnetism and Magnetic Materials, 2002, pp. 292-302, 241, No. 2.
Machine Translation of USSR Soviet Union Application No. SU1197658A1, published Dec. 15, 1985, retrieved from: https://patents.google.com/patent/SU1197658A1/en?oq=SU1197658A on Jul. 5, 2022, 4 pages.

* cited by examiner

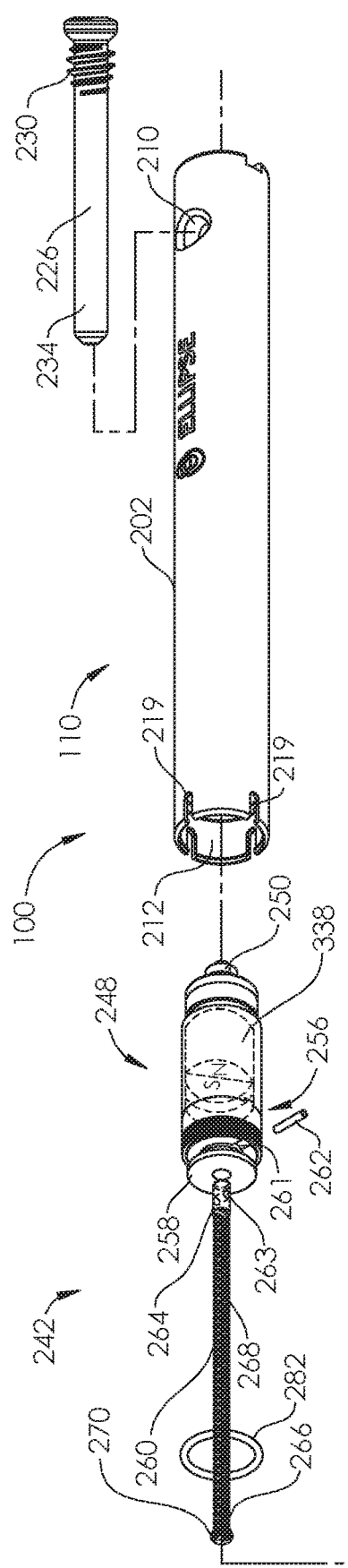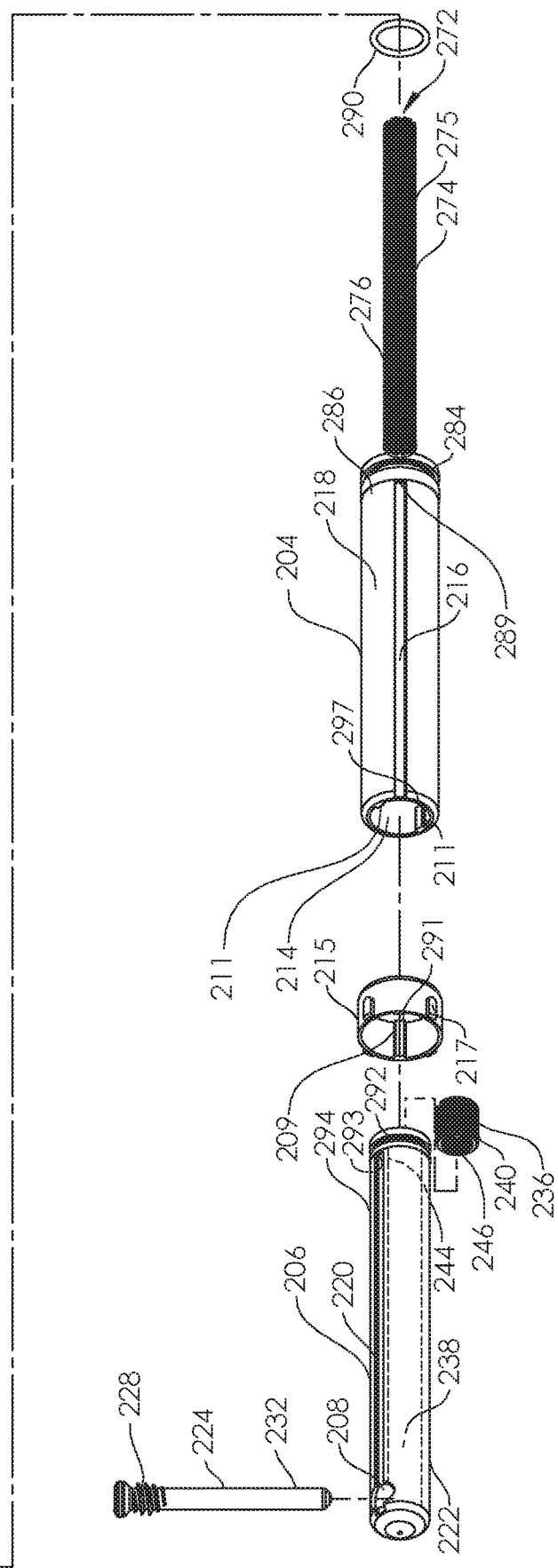
FIG. 4

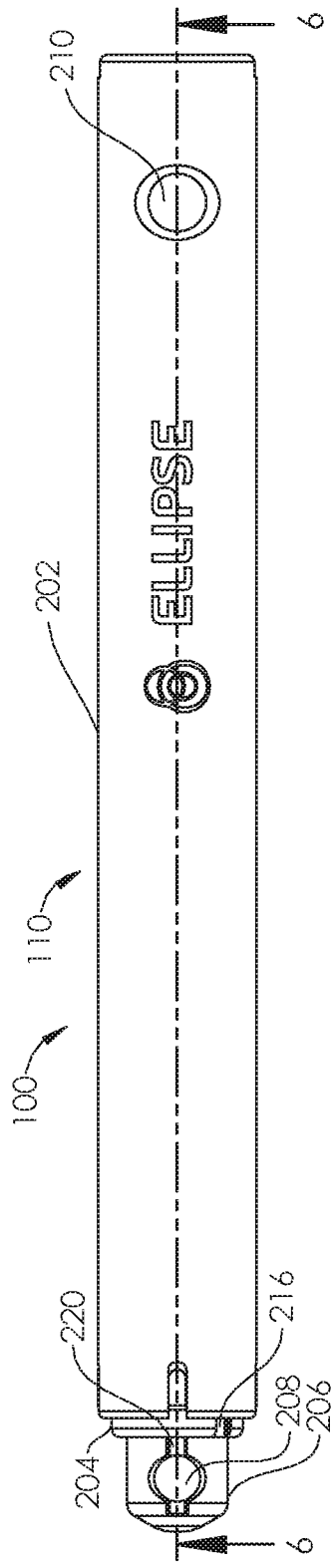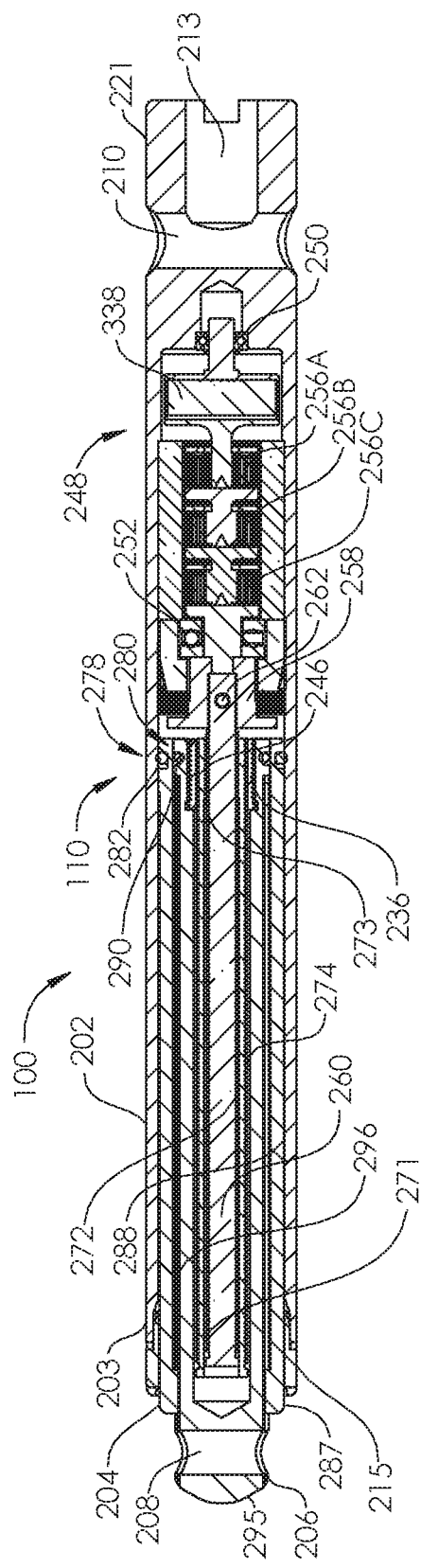
FIG. 5
FIG. 6

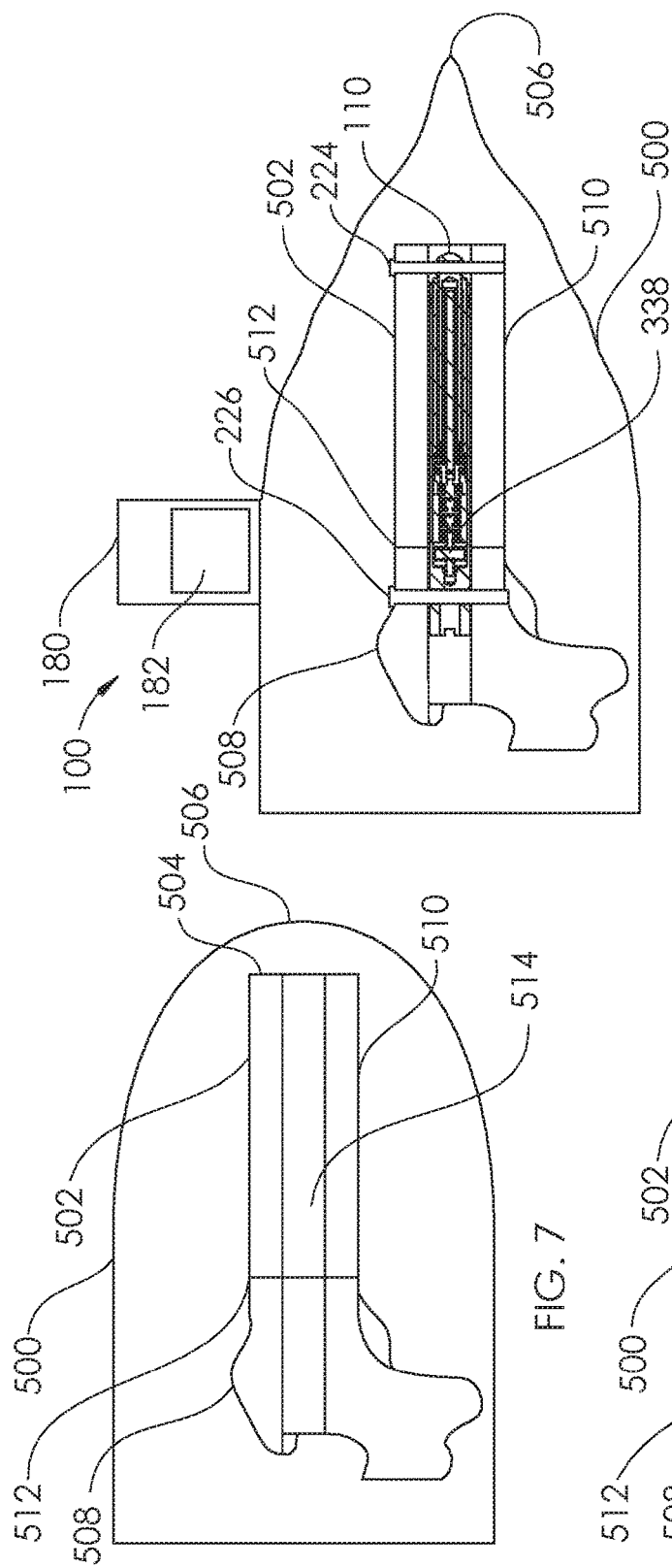
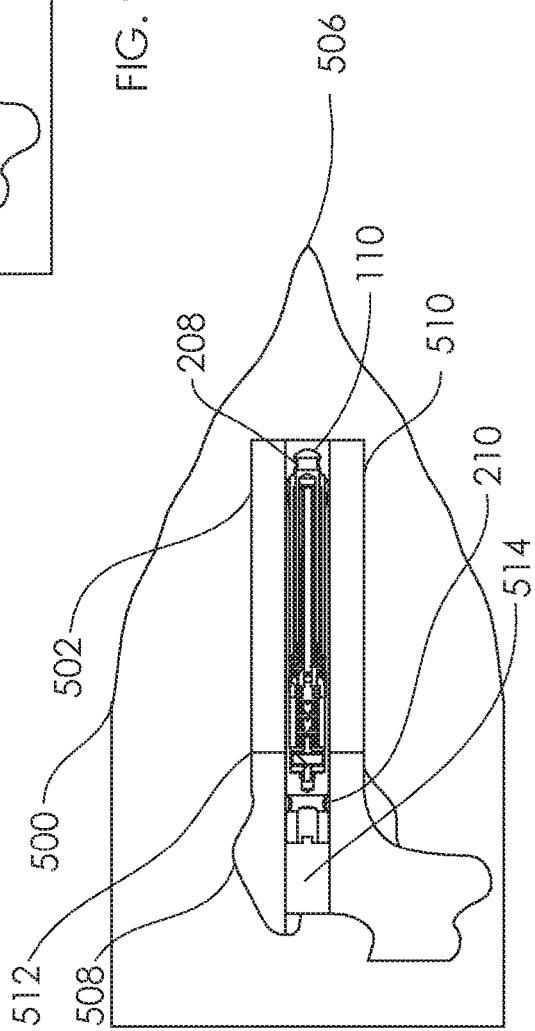
FIG. 7
FIG. 8
FIG. 9

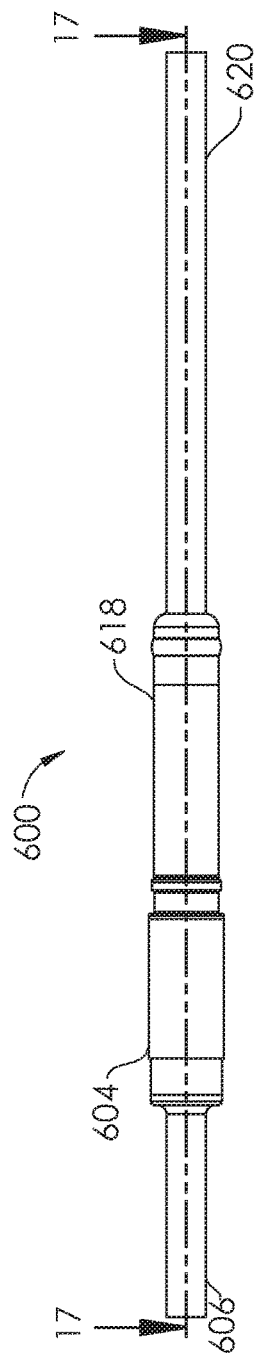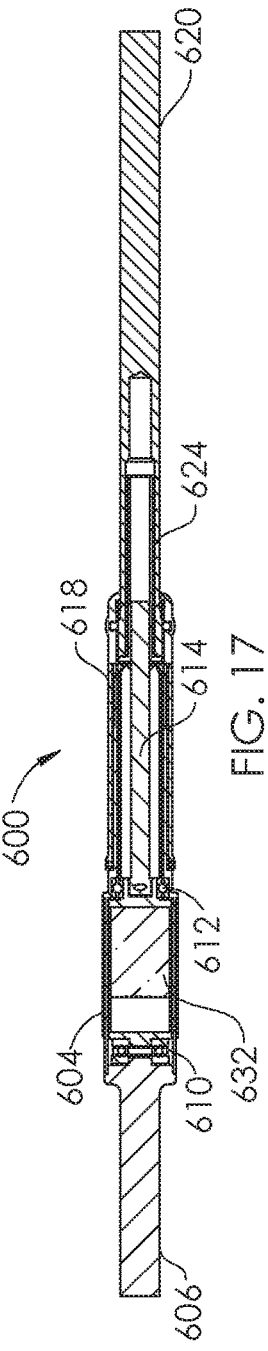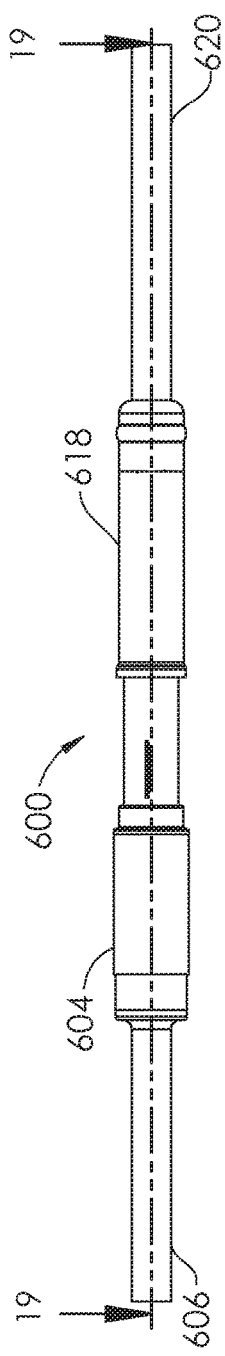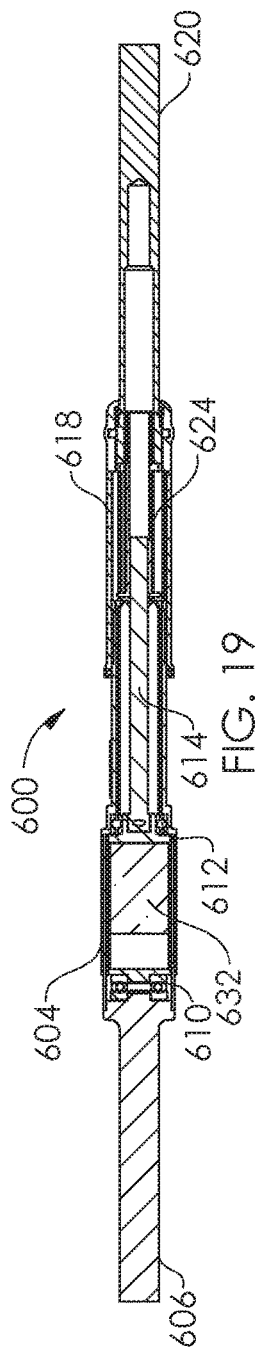

SYSTEMS AND METHODS FOR DISTRACTION

BACKGROUND

Any and all applications for which a foreign or domestic priority claim is identified in the Application Data Sheet as filed with the present application are hereby incorporated by reference under 37 CFR 1.57.

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation may actually create a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually monitored, often with subsequent x-rays. Patients with a Cobb angle of 40° or greater are frequently candidates for fusion surgery. It should be noted that many patients do not receive such a spinal assessment, for numerous possible reasons. Many school districts do not perform this simple assessment, and many children do not regularly visit a physician. Therefore, the curve often progresses rapidly and severely. There is a large population of grown adults with untreated scoliosis, some having extreme cases exhibiting Cobb angles of 90° or greater. Many adults having untreated scoliosis, though, do not have pain associated with their deformity and live relatively normal lives, though oftentimes with restricted mobility and motion. In AIS, the ratio of females to males having Cobb angles under 10° is about one to one. However, at Cobb angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section selected for fusion, the intervertebral disks are removed and bone graft material is placed to create the fusion. If autologous graft material is used, the bone is generally harvested from a hip via a separate incision.

Alternatively, fusion surgery may be performed anteriorly. A lateral d anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and secured to the vertebra on the anterior convex portion of the curve. Currently, clinical trials are being performed in which staples are used instead of the tether/screw combination. One advantage of this surgery in comparison with the posterior approach is that scars resulting from the several smaller incisions are not as dramatic, though they are still located in a visible area, when a bathing suit, for example, is worn. Staple-based techniques have experienced some difficulty in clinical trials. The staples tend to pull out of the bone when a critical stress level is reached.

In some cases, after surgery, the patient will wear a protective brace for a few months as the fusing process occurs. Once the patient reaches spinal maturity, it may be difficult to remove the rods and associated hardware in a subsequent surgery because the fusion of the vertebra usually incorporates the rods themselves. Therefore, standard practice is to leave this implant in for life. With either of these two surgical methods, after fusion the patient's spine is rendered straight, but, depending on the number of vertebrae that were fused, limitations in the degree of flexibility, both in bending and twisting, are often observed. As fused patients mature, the fused section of the spine can impart significant stresses on the adjacent non-fused vertebrae, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate, or at least reduce, one or more of the drawbacks of fusion.

One group of patients in which the spine is especially dynamic is the subset known as Early Onset Scoliosis (EOS), which typically occurs in children before the age of five, and more often in boys than in girls. EOS is a more rare condition than AIS, occurring in only about one or two out of 10,000 children, but can be severe, sometimes affecting the normal development of organs. Because the spines of these children will generally grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, or as required to match the child's growth, until the child is at least eight years old, and sometimes until they are 15 years old. Each adjustment requires a surgical incision to access the adjustable portion of the device. Because the patients may receive the device at an age as early as six months old, this treatment may require a large number of surgeries. Because of the multiple surgeries, these patients have a rather high incidence of infection.

Returning to the AIS patients, the treatment methodology for those with a Cobb angle between 20° and 40° is quite controversial. Many physicians prescribe a brace (for example, the Boston Brace) for a patient to wear on his body, under the clothes, 18 to 23 hours a day until the patient become skeletally mature age 16). Because these patients are all passing through their socially demanding adolescent years, it is a quite serious prospect to choose between wearing a somewhat bulky brace that covers most of the upper body, having fusion surgery that may leave large scars and limit motion, and doing nothing and risking becoming disfigured and possibly disabled. It is common knowledge that many patients have, at times, hidden their braces, for example, in a bush outside of school, in order to escape embarrassment associated with the brace(s). The patient compliance with brace wearing has been so problematic that special braces have been constructed that sense the body of the patient and keep track of the amount of time per day that the brace is worn. Even such special braces have problems with patient compliance: patients have been known to place objects into unworn braces of this type in order to tool the sensor. Coupled with the inconsistent patient compliance with brace usage, is a feeling by many physicians that braces, even if used properly, are not at all effective at curing scoliosis. Physicians may agree that bracing can possibly slow down or even temporarily arrest curve (Cobb angle) progression, but they have noted that as soon as the treatment period ends and the brace is no longer worn, often the scoliosis progresses rapidly to a Cobb angle even more severe than it was at the beginning of treatment. Some say the reason for the supposed ineffectiveness of the brace is that it braces only on a portion of the torso, and not on the entire spine. Currently a prospective, randomized, 500-patient, clinical trial known as BrAIST (Bracing in Adolescent idiopathic Scoliosis Trial) is enrolling patients, 50% of whom will be treated with the brace and 50% of who will simply be watched. Cobb angle data from these patients will be measured continually up until they reach skeletal maturity, or until a Cobb angle of 50° is reached, at which time the patient will likely undergo surgery. Many physicians feel that the BrAIST trial will show that braces are completely ineffective. If this is the case, the quandary about what to do with AIS patients who have a. Cobb angle of between 20° and 40° will only become more pronounced. It should be noted that the patient population having a Cobb angle of 20-40° is as much as ten times larger than the population having a Cobb angle of 40° and greater.

Distraction osteogenesis, also known as distraction callotasis and osteodistraction has been used successfully to lengthen various bones of the body (e.g., long bones). Typically, the bone, if not already fractured, is purposely fractured by means of a corticotomy, and the resulting two segments of bone are gradually distracted apart, thereby allowing new bone to form in the gap. If the distraction rate is too high, there is a risk of nonunion. If the rate is too low, there is a risk that the two segments will prematurely, fuse to each other more than desired before the distraction period is complete. Once the desired length of the bone is achieved using this process, the bone is allowed to consolidate. Distraction osteogenesis applications are mainly focused on the growth of the femur or tibia, but may also include the humerus, the jaw bone (micrognathia), or other bones. There are many reasons for lengthening or growing bones which may be desirable. The applications including, but not limited to: post osteosarcoma bone cancer; cosmetic lengthening (both legs-femur and/or tibia) in short stature or dwarfism/achondroplasia; lengthening of one limb to match the other (congenital, post-trauma, post-skeletal disorder, prosthetic knee joint), nonunions.

Distraction osteogenesis using external fixators has been done for many, years, but the external fixator can be unwieldy and painful for the patient. It can also subject the patient to the risk of pin track infections, joint stiffness, loss of appetite, depression, cartilage damage and other side effects. An external fixator, e.g., around the patient/patient's limb, can also delay the beginning of rehabilitation.

In response to the shortcomings of external fixator distraction, intramedullary distraction nails which may be contained entirely within the bone have, been surgically implanted. Some such nails may be automatically lengthened via repeated rotation of the patient's limb, which can sometimes be painful to the patient, and can often proceed in an uncontrolled fashion. This therefore makes it difficult to follow the strict daily or weekly, lengthening regime that avoids nonunion (if too fast) or early consolidation (if too slow). Lower limb distraction rates are generally on the order of about one mm per day. Other intramedullary nails which have an implanted motor and may be remotely controlled by an antenna have also been developed. These devices are designed to be lengthened or distracted in a controlled manner, but, due to their complexity, may not be manufacturable as an affordable product. Others have proposed intramedullary distracters containing an implanted magnet, which allows the distraction to be driven electromagnetically by an external stator. Because of the complexity and size of the external stator, this technology has not been reduced to a simple and/or cost-effective device, which can be taken home to allow patients to do daily lengthenings. Non-invasively adjustable implantable distraction devices, at least one embodiment of which is magnetically non-invasively adjustable, have been developed and used clinically in both scoliosis and limb lengthening patients.

Knee osteoarthritis is a degenerative disease of the knee joint that affects a large number of patients, particularly over the age of 40. The prevalence of this disease has increased significantly over the last several decades, attributed partially, but not completely, to the rising age of the population as well as the increase in obesity. The increase may also be due to an increase in highly active people within the population. Knee osteoarthritis is caused mainly by long term stresses on the knee that degrade the cartilage covering the articulating surfaces of the bones in the knee joint. Oftentimes, the problem becomes worse after a particular trauma event, but it can also be a hereditary process. Symptoms include, but are not limited to, pain, stiffness, reduced range of motion, swelling, deformity, and muscle weakness. Osteoarthritis may include one or more of the three compartments of the knee: the medial compartment of the tibiofemoral joint, the lateral compartment of the tibiofemoral joint, and the patellofemoral joint. In severe cases, partial or total replacement of the knee is performed in order to replace the diseased portions with new weight bearing surfaces for the knee, typically made from implant grade plastics or metals. These operations may involve significant post-operative pain and require substantial physical therapy. The recovery period may last weeks or months. Several potential complications of this surgery exist, including deep venous thrombosis, loss of motion, infection, and bone fracture. After recovery, surgical patients who have received uni-compartmental or total knee replacement, must significantly reduce their activity, removing running and high energy sports completely from their lifestyle.

For these reasons, surgeons are attempting to intervene early in order to delay or even preclude knee replacement surgery. Osteotomy surgeries may be performed on the femur or tibia, in order to change the angle between the femur and tibia, and thus adjust the stresses on the different portions of the knee joint. In closed wedge or closing wedge osteotomy, an angled wedge of bone is removed, and the remaining surfaces are fused together, creating a new improved bone angle. In open wedge osteotomy, a cut is made in the bone and the edges of the cut are opened, creating a new angle. Bone graft is often used to fill in the newly-opened, wedge-shaped space, and, often, a plate is attached to the bone with bone screws. Obtaining the correct angle during either of these types of osteotomy is almost always difficult, and, even if the final result is close to what was desired, there can be a subsequent loss of the correction angle. Some other complications associated with this technique include nonunion and material failure.

Amputation of the arm or the leg can result in a residual limb, with a stump, having a shortened bone (e.g., a shortened femur, tibia, fibula, humerus, radius or ulna). A prosthetic limb or prosthetic limb attachment which may be attached to a residual limb may have problems fitting or functioning when attached to a residual limb having insufficient bone length. There may be poor energy transfer between the residual limb and the attached prosthesis, as short lever arms generate less torque for a given force. This functional deficit is compounded when the lever arm is encased in very compliant tissue, such as a residual femur that is surrounded by the soft tissues of the thigh. This may further impair prosthesis control. Individuals having short residual limbs may display gait asymmetries and gait changes. The wearer of a prosthetic limb who has a relatively short residual limb may exhibit compensatory changes that affect posture and cause discomfort or injury to the spine or other body structures. Amputation may occur or may be performed for several reasons including war-related injuries, motor vehicle accidents, including motorcycle accidents, other types of trauma or cancer of the bone or other adjacent tissue.

In addition to the many different types of implantable distraction devices that are configured to be non-invasively adjusted, implantable non-invasively adjustable non-distraction devices have also been envisioned, for example, adjustable restriction devices for gastrointestinal disorders such as GERD, obesity, or sphincter laxity (such as in fecal incontinence), or other disorders such as sphincter laxity in urinary incontinence. These devices, too, may incorporate magnets to enable non-invasive adjustment.

SUMMARY

The present disclosure provides for a system for moving a portion of a patient's body including a housing having a first cavity extending along a longitudinal axis, a first distraction rod having a proximal end and a distal end and configured to be telescopically displaceable from within the first cavity along the longitudinal axis, the first distraction rod having a second cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

The present disclosure further provides for a method of modifying a residual limb of a patient including the steps of providing a distraction device having a housing extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and being configured to be telescopically displaceable from within the cavity along the longitudinal axis, and a drive system configured to move the first distraction rod in relation to the housing and to move the second distraction rod in relation to the first distraction rod, attaching the housing to a first portion of a bone within the residual limb, attaching the second distraction rod to a second portion of the bone within the residual limbo decoupling the first portion of the bone from the second portion of the bone, and wherein the distraction device is actuatable such that the first distraction rod is caused to move in relation to the housing and the second distraction rod is caused to move in relation to the first distraction rod, to increase at least one of a force or a distance between the first portion of the bone and the second portion of the bone.

The present disclosure further provides for a system for moving a portion of a patient's body including a housing having a first cavity extending along a longitudinal axis, a first distraction rod having a proximal end and a distal end, the first distraction rod and the housing being telescopically displaceable with respect to each other along the longitudinal axis, the first distraction rod having a cavity extending along the longitudinal axis, a second distraction rod having a proximal end and a distal end and configured to be telescopically displaceable from within the second cavity along the longitudinal axis, and a drive system configured to move the first distraction rod in relation to the housing and to move the second distraction rod in relation to the first distraction rod.

In one embodiment, a system for moving a portion of a patient's body is provided. The system for moving a portion of a patient's body includes: a housing having a first cavity extending along a longitudinal axis; a first distraction rod having a proximal end, a distal end, and a second cavity extending between the proximal end and the distal end, and being configured for telescopic displacement from within the first cavity; a second distraction rod having a proximal end and a distal end, and being configured for telescopic displacement from within the second cavity; and a drive system configured to move at least one of the first distraction rod and the second distraction rod.

In one embodiment, a method of modifying a residual limb is provided. The method of modifying a residual limb of a patient includes the steps of: providing a distraction device comprising: a housing extending along a longitudinal axis; a first distraction rod having a proximal end and a distal end, the first distraction rod and the housing being telescopically displaceable with respect to each other, the first distraction rod having a cavity extending along the longitudinal axis; a second distraction rod having a proximal end and a distal end and configured to be telescopically displaceable from within the cavity; and a drive system configured to move at least one of the first distraction rod in relation to the housing and the second distraction rod in relation to the first distraction rod; decoupling the first portion of the bone from the second portion of the bone; attaching the housing to a first portion of a bone within the residual limb; attaching the second distraction rod to a second portion of the bone within the residual limb, wherein the distraction device is actuatable such that the first distraction rod is caused to move in relation to the housing and the second distraction rod is caused to move in relation to the first distraction rod, to increase at least one of a force or a distance between the first portion of the bone and the second portion of the bone.

In another embodiment, a system for moving a portion of a patient's body is provided. The system for moving a portion of a patient's body includes: a housing having a first cavity extending along a longitudinal axis; a first distraction rod having a proximal end, a distal end, and a cavity extending along the longitudinal axis, the first distraction rod and the housing being telescopically displaceable with respect to each other along the longitudinal axis; a second distraction rod having a proximal end and a distal end, and configured to be telescopically displaceable from within the second cavity along the longitudinal axis; a drive system configured to move the first distraction rod in relation to the housing and to move the second distraction rod in relation to the first distraction rod.

In still another embodiment, a system for moving a portion of a patient's body is provided. The system for moving a portion of a patient's body includes: a housing having a first cavity; a first distraction rod having a proximal end, a distal end, and a second cavity, wherein the first distraction rod is configured for telescopic displacement relative to the first cavity; a second distraction rod having a proximal end and a distal end, wherein the second distraction rod is configured for telescopic displacement from within the second cavity; and a drive system configured to move at least one of the first distraction rod and the second distraction rod.

In one embodiment, a method of modifying a residual limb of a patient is provided. The method of modifying a residual limb includes the steps of: providing a distraction device comprising: a housing having a first cavity; a first distraction rod having a proximal end, a distal end, and a second cavity, wherein the first distraction rod is telescopically displaceable relative to the first cavity; a second distraction rod having a proximal end and a distal end, wherein the second distraction rod is telescopically displaceable from within the second cavity; and a drive system configured to move at least one of the first distraction rod and the second distraction rod with respect to the housing; then decoupling a first portion of a bone within the residual limb from a second portion of the bone; attaching the housing to one of the first portion and the second portion of the bone within the residual limb; and attaching the second distraction rod to the other of the first portion and the second portion of the bone within the residual limb, wherein the drive system is configured to be actuated so as to increase at least one of a force and a distance between the first portion and the second portion of the bone.

BRIEF DESCRIPTION OF THE DRAWINGS

FIG. 4 illustrates air exploded view of a distraction device.
FIG. 5 illustrates an elevation view of a distraction device.
FIG. 6 illustrates a sectional view of the distraction device of FIG. 5 taken along line 6-6.
FIG. 7 illustrates a residual limb.
FIG. 8 illustrates a distraction device inserted within a medullary canal of a bone of a residual limb.
FIG. 9 illustrates a distraction device secured within a medullary canal of a hone of a residual limb.

FIG. 16 illustrates the distraction device of FIGS. 14 and 15 in a partially distracted configuration.
FIG. 17 illustrates a sectional view of the distraction device of FIG. 16 taken along line 17-17.
FIG. 18 illustrates the distraction device of FIGS. 14-17 in a fully distracted configuration.
FIG. 19 illustrates a sectional view of the distraction device of FIG. 18 taken along line 19-19.

DETAILED DESCRIPTION

Embodiments of the adjustable devices for implanting into the body disclosed herein are capable of achieving a large (e.g., greater than 40%, greater than, greater than 60%, greater than 80%, greater than 100% and even greater than 120%) total amount of adjustment length in comparison to the total length of the adjustable portion of the device. Adjustable devices may include distraction devices, for example distraction devices for orthopedic applications, including, but not limited to scoliosis, limb lengthening, bone transport, spinous process distraction, tibial wedge osteotomy adjustment, and spondylolisthesis. Maintaining a small size an adjustable (e.g., distraction and/or retraction) implant to fit into a small, short space within the body, and achieving large amounts of adjustable length have historically been conflicting design goals.

Figure 1:
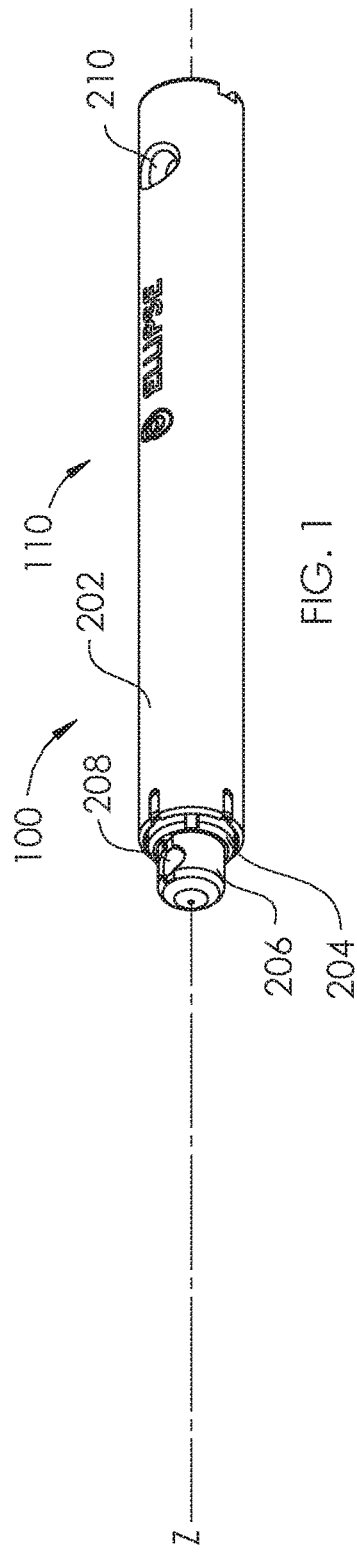
FIG. 1 is a perspective view of a distraction device.
Figure 2:
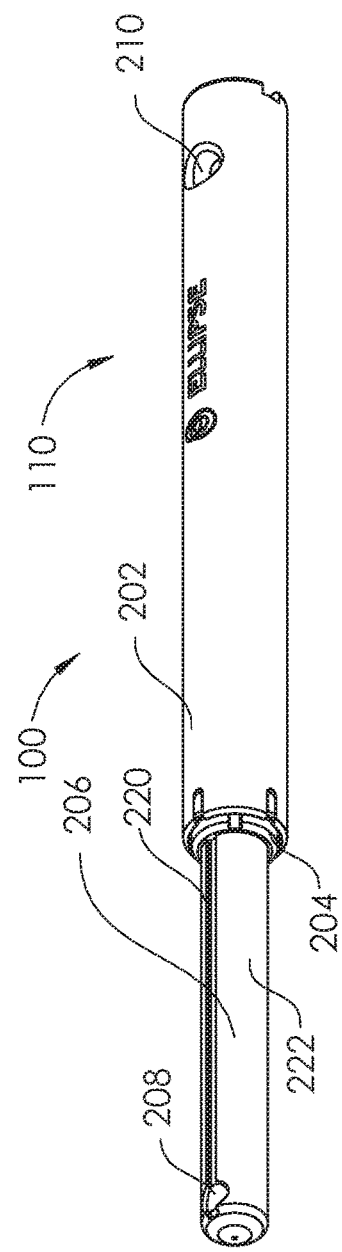
FIG. 2 illustrates the distraction device of FIG. 1 in a partially distracted configuration.
Figure 3:
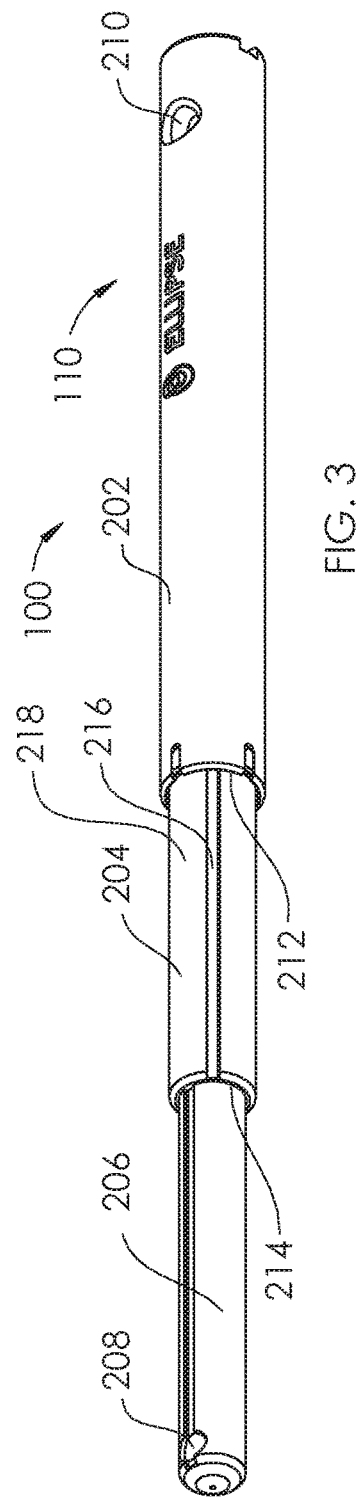
FIG. 3 illustrates the distraction device of FIG. 1 in a fully distracted configuration.

FIGS. 1-3 illustrate an embodiment of an implantable adjustable system 100 comprising a distraction device 110. The distraction device 110 comprises a housing 202, a first distraction rod 204 and a second distraction rod 206. The second distraction rod 206 and the housing 202 are each configured for coupling to a patient. The second distraction rod 206 contains one or more holes 208 for passing an anchor with which to secure the distraction device 110 to a patient. One of the one or more holes 208 may be located between about 3 mm and 15 mm, or approximately 5 mm, from the distal end of the second distraction rod 206. The housing 202 contains one or more holes 210 for passing an anchor with which to secure the distraction device 110 to the patient. One of the one or more holes 210 may be located between about 5 mm and about 20 mm, or approximately 10 mm, from the proximal end of the housing 202. The housing 202 may have a diameter of between about 8.5 mm and about 16 mm, or between about 10.5 mm and about 14.5 mm, or about 14 mm. In some embodiments, the anchor is a bone anchor, for example, a bone screw 224, 226 (FIG. 4). The bone screws 224, 226 may be between about 3 mm and about 6 mm in diameter. In some embodiments, bone screw 244 is 4 mm in diameter and bone screw 226 is 5 mm in diameter. The bone screws may be between about 18 mm and about 80 mm in length, or between about 20 mm and about 75 mm in length. However, other types of anchoring and/or connection are contemplated for coupling the second distraction rod 206 and the housing 202 to the bone of the patient. As illustrated in FIG. 2, the second distraction rod 206 may be configured to be telescopically displaceable with respect to the housing 202. As seen in FIG. 2, the second distraction rod 206 may be configured to also be telescopically displaceable with respect to the first distraction rod 204. As illustrated in FIG. 3, the first distraction rod 204 may be configured to be telescopically displaceable with respect to the housing 202. The first distraction rod 204 may be longitudinally displaceable from within a cavity 212 in the housing 202 that extends along longitudinal axis Z (FIG. 1). The first distraction rod 204 may be configured to be telescopically displaceable along the longitudinal axis Z. The first distraction rod 204 has a cavity 214, with the second distraction rod 206 configured to telescopically displace from the cavity 214 along the longitudinal axis Z. In some embodiments, the first distraction rod 204 may have a diameter of between about 8 mm and about 13 mm, or about 11.5 mm. In some embodiments, the second distraction rod 206 may have a diameter of between about 5 mm and about 11 mm, or about 9 mm. In some embodiments it may be desired that there be no rotational motion (about the longitudinal axis Z) between at least one of the housing 202, the first distraction rod 204, and the second distraction rod 206. In some embodiments, one or more first longitudinal grooves 216 extends along an exterior surface 218 of the first distraction rod 204 and is slidingly engaged by protrusions 209 (FIG. 4) which extend in an inward radial direction from the interior of a cap 215, which is coupled to the housing 202, thus allowing longitudinal displacement between the first distraction rod 204 and the housing 202, but not allowing rotation between them. External ribs 217 on the cap 215 insert into grooves 219 in the housing 202 during assembly. The cap 215 may be snapped into place on the housing 202 or otherwise secured by adhesive, welding, soldering, brazing or other methods. One or more second longitudinal grooves 220 extending along an exterior surface 222 of the second distraction rod 206 are slidingly engaged by protrusions 211 (FIG. 4) which extend from the interior of the cavity 214 of the first distraction rod 204 in an inward radial direction, thus allowing longitudinal displacement between the second distraction rod 206 and the first distraction rod 204, but not allowing rotation between them. If the distraction device 110 is used for the purpose of distracting two pieces of bone (e.g., move two bones or two pieces of a bone apart from each other), then the protrusions 209, 211 and longitudinal grooves 216, 220 make it possible to assure that there may be substantially no rotation between the two bone pieces. As seen in FIG. 3, the first longitudinal grooves 216 and the second longitudinal grooves 220 can be purposely configured to reside at different clock positions (in circumferential relation to the longitudinal axis Z (FIG. 1), in order to make enough room in the second distraction rod 206, the first distraction rod 204, and the housing 202, so that wall thickness, and thus strength and durability, are not compromised.

Turning to FIG. 4, bone screws 224, 226 are depicted having unicortical threads 228, 230 and unthreaded shafts 232, 234, however, any type of bone screw, for example a fully-threaded hone screw, may be used for placement through the holes 208, 210. The holes 208, 210 may be perpendicular to the longitudinal axis Z, or may be at various angles, depending upon the configuration through which they are to be coupled to the bone. With further reference to FIGS. 4-6, the distraction device 110 comprises a driving element 242 configured to be activated by a remotely applied source. A nut 236 may be secured within a cavity 238 in the second distraction rod 206. The nut 236 may have external threads 240, which are engaged or bonded into an internal thread 244 of the cavity 238. The nut 236 also contains an internal thread 246. A magnetic assembly 248 may be held between a radial bearing 250 and a thrust bearing 252 (FIG. 6), and comprises a radially-poled permanent magnet 338 which is rotationally coupled to one or more gear modules 256 (e.g., planetary gearing). The thrust bearing 252 and radial bearing 250 may be restrained at their longitudinal extents in relation to the housing 202, in order to maintain the magnetic assembly 248 within the housing 202, while allowing it and its components to rotate freely. In some embodiments, the permanent magnet 338 may be carried within one or more cylindrical housings or cups. The one or more gear modules 256 output (through the interior of the thrust bearing 252) to a coupler 258, which may be rotationally coupled to a first lead screw 260 via a pin 262, which passes through a hole 261 in the coupler 258 and a hole 263 at a proximal end 264 of the first lead screw 260. The first lead screw 260 also has an abutment 270 at its distal end 266, and comprises an external thread 268. In some embodiments, the gear modules 256 may provide a gear ratio of 4:1, 16:1, 64:1, 256:1 between the magnet 338 and the first lead screw 260, or another ratio. In some embodiments, the first lead screw 260 may be directly coupled to the magnet 338, and thus provide 1:1 rotation. The first lead screw 260 may be threadingly engaged with an internal thread 272 of a second lead screw 274. The majority of the length of the second lead screw 274 may be an internal bore 271 with a diameter that is equal to or greater than the major diameter of the internal thread 272. The internal thread 272 may be located only at the proximal end 275 of the second lead screw 274. In some embodiments, the length of the internal thread 272 along the longitudinal axis Z may be about 3 mm to about 7 mm, or about 5.5 mm. The external thread 276 of the second lead screw 274 may be threadingly engaged with the internal thread 246 of the nut 236 which may be secured within the second distraction rod. An exemplary external thread specification for each of the lead screws 260, 274 may be 80 threads per inch.

The interior contents of the distraction device 110, including the interior portions of cavities 212, 214, 238, which contain the magnetic assembly 248 and the lead screws 260, 274, are protected from external fluids and materials by dynamic seals 278, 280. A first dynamic seal 278 includes an o-ring 282, which resides within a circumferential groove 284 at a proximal end 286 of the first distraction rod 204. The o-ring 282 seals along an inner cylindrical surface 288 of the housing 202, and maintains the dynamic seal 278 throughout the longitudinal displacement of the first distraction rod 204 with the housing 202. A second dynamic seal 280 includes an o-ring 290, which resides within a circumferential groove 292 at a proximal end 294 of the second distraction rod 206. The o-ring 290 seals along an inner cylindrical surface 296 of the first distraction rod 204, and maintains the dynamic seal 280 throughout the longitudinal displacement of the second distraction rod 206 with the first distraction rod 204.

Figure 12:
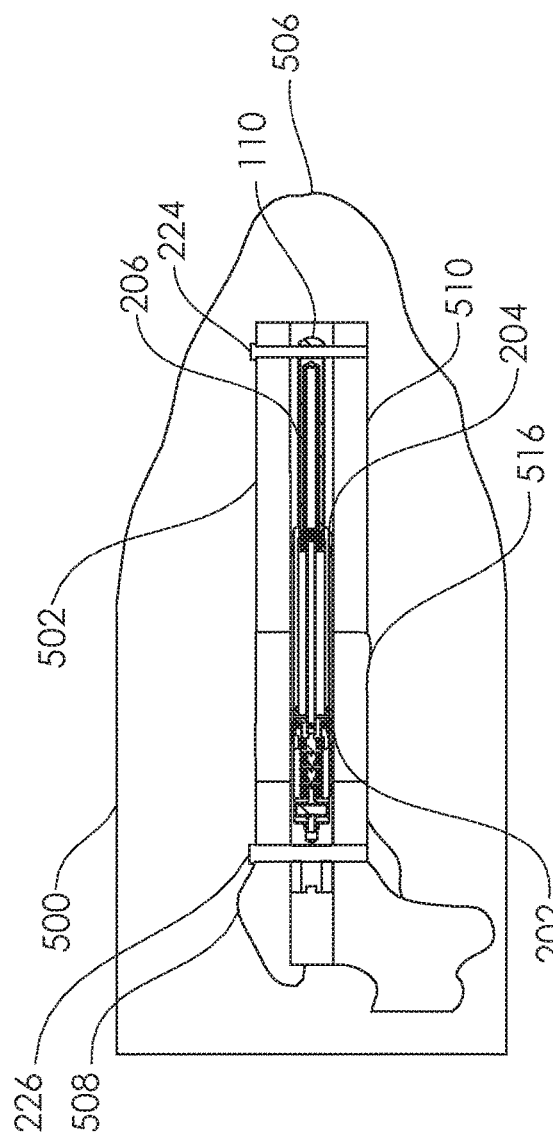
FIG. 12 illustrates a distraction device and residual limb after partial distraction.

FIG. 6 illustrates the distraction device 110 in a fully undistracted (or retracted) condition, wherein the distal end 287 of the first distraction rod 204 and the distal end 295 of the second distraction rod 206 are located near the distal end 203 of the housing 202. In use, when the magnet 338 is rotated (e.g., by an externally-applied moving magnetic field) (and caused to rotate in a first rotational direction) the first lead screw 260 may be turned (through the gear ratios of gear modules 256A, 256B, 256C). The turning of the external thread 268 of the first lead screw 260 in relation to the internal thread 272 of the second lead screw 274, thus causes both the second distraction rod 206 and the second lead screw 274 to longitudinally extend from the housing 202. As described, in at least some embodiments, the second distraction rod 206 is prevented from rotation with respect to the first distraction rod 204 and the housing 202. In some embodiments, the second lead screw 274 does not turn as it longitudinally extends with the second distraction rod 206, thus the first distraction rod 204 does not longitudinally extend in relation to the housing 202. FIG. 12, which will be referred to later when describing the procedure for lengthening a bone in a residual limb, shows the distraction rod 110 after the second distraction rod 206 has been longitudinally extended in relation to both the housing 202 and the first distraction rod 204. For this first stage of distraction to occur as described, the frictional torque between the external thread 268 of the first lead screw 260 and the internal thread 272 of the second lead screw 274 is less than the frictional torque between the external thread 276 of the second lead screw 274 and the internal thread 246 of the nut 236. This tends to be the case, however, other assembly steps and materials may additionally be provided in order to assure this. For example, in some embodiments, a silicone lubricant or a Krytox® lubricant may be applied to the external thread 268 of the first lead screw 260 and/or the internal thread 272 of the second lead screw 274, but not to the external thread 276 of the second lead screw 274 and the internal thread 246 of the nut 236. In some embodiments, the lubricant may be applied more liberally to the external thread 268 of the first lead screw 260 and/or the internal thread 272 of the second lead screw 274 than to the external thread 276 of the second lead screw 274 and/or the internal thread 246 of the nut 236. In some embodiments, a more lubricious lubricant may be applied to the external thread 268 of the first lead screw 260 and/or the internal thread 272 of the second lead screw 274 while a less lubricious lubricant is applied to the external thread 276 of the second lead screw 274 and/or the internal thread 246 of the nut 236.

Figure 13:
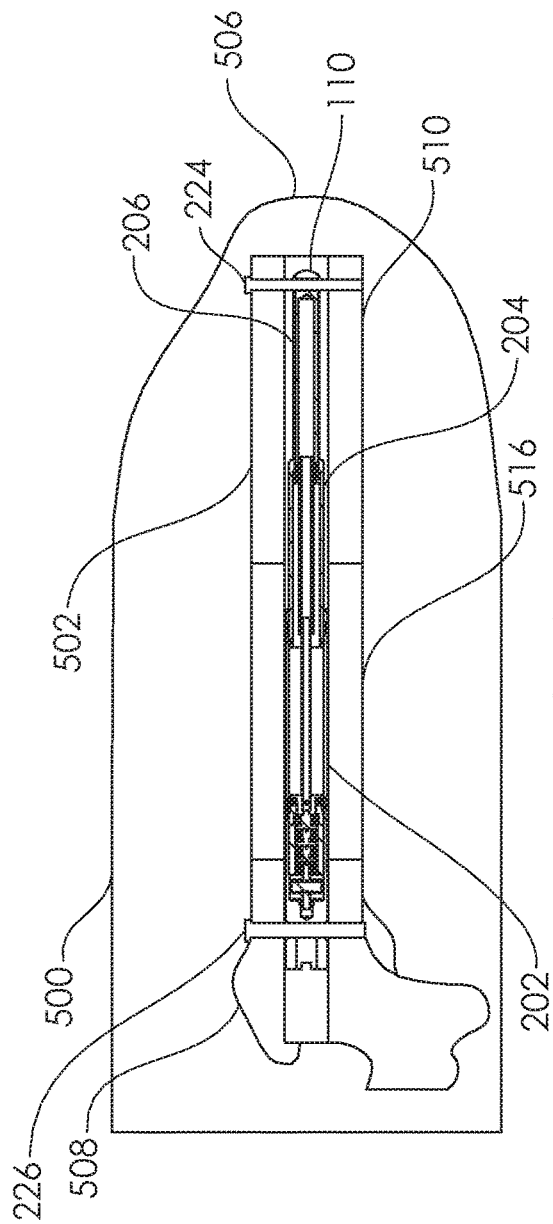
FIG. 13 illustrates a distraction device and residual limb after full distraction.

The longitudinal length of distraction possible for the second distraction rod 206 on its own may be between about 20 mm and about 90 mm, or between about 40 mm and about 70 mm, or about 50 mm. When the second distraction rod 206 has been fully distracted in relation to the first distraction rod 204, the first lead screw 260 will rotationally engage with the second lead screw 274, and thus the rotation of the first lead screw 260 will begin to turn the second lead screw 274 (e.g., in a one-to-one manner). In some embodiments, this occurs when the abutment 270 at the distal end 266 of the first lead screw 260 contacts a ledge 273 adjacent the internal thread 272 at the proximal end 275 of the second lead screw 274. As the first lead screw 260 continues to turn the second lead screw 274, the external thread 276 of the second lead screw 274 turns inside the internal thread 246 of the nut 236 of the second distraction rod 206, causing the second distraction rod 206 to longitudinally extend further in relation to the housing 202, but now, while also dragging the first distraction rod 204 along with it. The longitudinal length of distraction possible for the first distraction rod 204, after full distraction of the second distraction rod 206, may be between about 20 mm and about 90 mm, or between about 40 mm and about 70 mm, or about 50 mm. FIG. 13 shows the distraction rod 110 after the first distraction rod 204 and the second distraction rod 206 have been longitudinally extended in this manner in relation to the housing 202. Using this two-stage approach to distraction, a total distraction length of 100 mm, or even greater than 100 mm, may be possible with a housing 202 having a cavity 212 length of only 97 mm; thus the distraction length provided can be 102% of the housing cavity length. In some embodiments, the length of the distraction device 110 is 130 mm in a fully retracted state and 230 mm in a fully distracted state. Prior art devices that use only a single distraction rod generally provide distraction lengths of only 40% to 50% of the housing cavity length. The distraction device 110 may be also capable of retracting, by applying a moving magnetic field in an opposite direction, and causing the components to turn in opposite directions.

In some embodiments, the distraction device 110 (FIG. 4) may include features to limit the extent of distraction of the second distraction rod 206 in relation to the first distraction rod 204, and in the first distraction rod 204 in relation to the housing 202. For example, an abutment 289, or stop, may be located at the end of the longitudinal groove 216, or at another location at the proximal end 286 of the first distraction rod 204. An abutment 291, or stop, may be located at a distal, internal portion of the housing 202, For example, wherein the abutment 291 is a protrusion carried on the internal wall of the housing 202, or wherein it is a one end of the protrusion 209 of the cap 215. The abutment 291 may be configured to abut/engage the abutment 289 at a maximum degree of extension of the first distraction rod 204 in relation to the housing 202. Furthermore, an abutment 293, or stop, may be located at the end of the longitudinal groove 220, or at another location at the proximal end 294 of the second distraction rod 206. An abutment 297, or stop, may be located at a distal, internal portion of the first distraction rod 204, for example, wherein the abutment 297 is a protrusion carried on the internal wall of the first distraction rod 204. The abutment 297 may be configured to abut/engage the abutment 293 at a maximum degree of extension of the second distraction rod 206 in relation to the first distraction rod 204. Each of the abutments 289, 291, 293, 297 may be configured so that the second distraction rod 206, the first distraction rod 204, and the housing 202 do not get stuck or jammed against each other when the longitudinal extents are reached, thus allowing for retraction or shortening of the distraction device 110, if desired. The shortening of the distraction device 110 may be desired in certain situations in which compression of bone pieces is needed. This includes situations in which it is desired to form, reform, or improve a callus for osteogenesis. In some embodiments, the protrusions 209, 211 themselves may serve as the abutments 291, 297.

Figure 10:
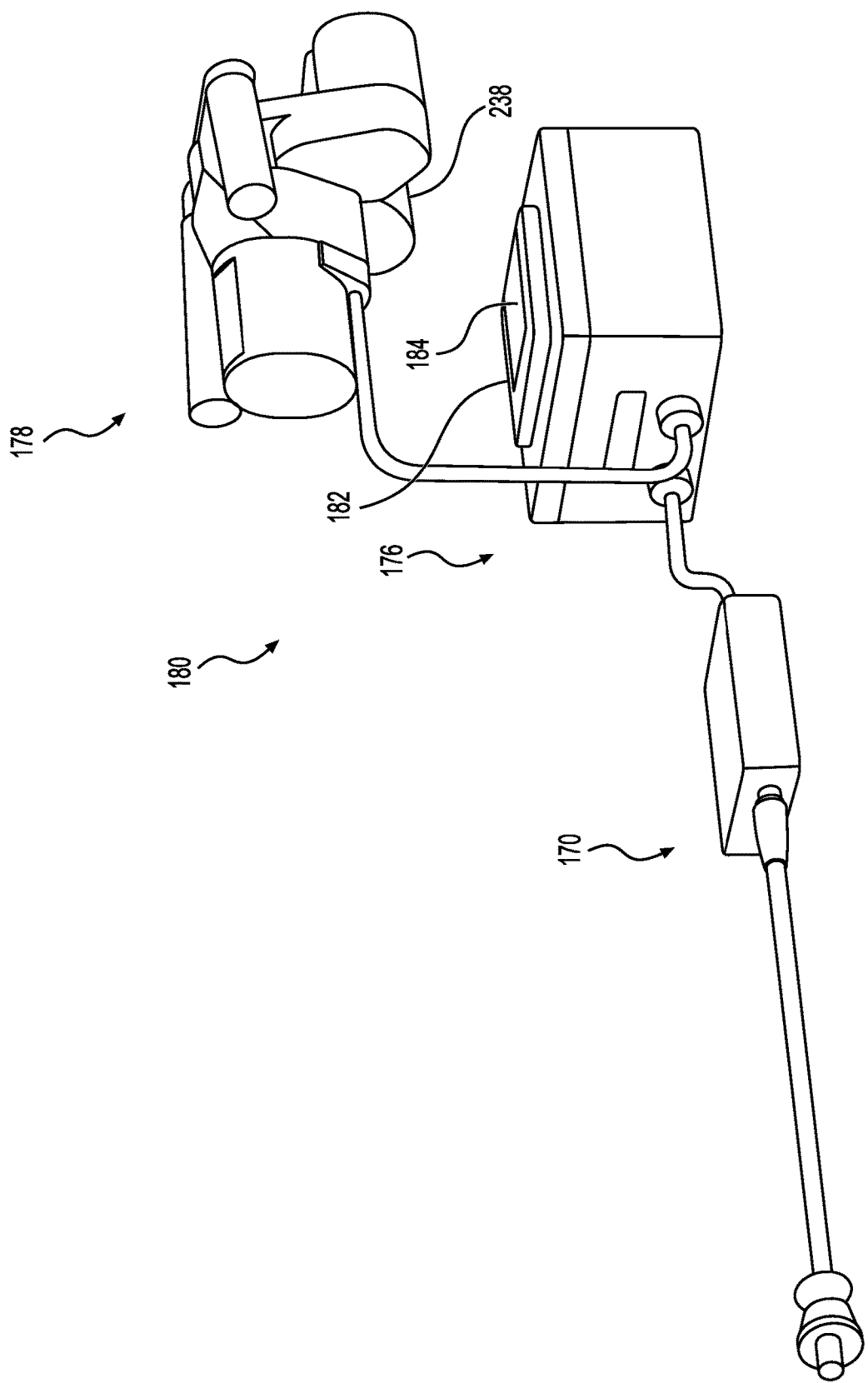
FIG. 10 illustrates an example external remote controller for wirelessly controlling and communicating with an implantable device.

The implantable adjustable system 100 incorporating a distraction device 110, as disclosed herein, may utilize an External Remote Controller (ERC). FIG. 10 illustrates an example of an External Remote Controller (ERC) 180 which may be used to non-invasively control the distraction device 110 by means of a magnetic coupling of torque. ERC 180 comprises a magnetic handpiece 178, a control box 176 (containing a processor) which may be integrated with the handpiece 178 and a power supply 174 such as a battery or external plug for connection to a standard power outlet. The control box 176 includes a control panel 182 having one or more controls (buttons, switches or tactile, motion, audio or light sensors) and a display 184. The display 184 may be visual, auditory, tactile, the like, or some combination of the aforementioned features, or any other display/UI described in this disclosure. The control box 176 may further contain a transceiver for communication with a transceiver in the implant and/or other external devices.

Figure 11:
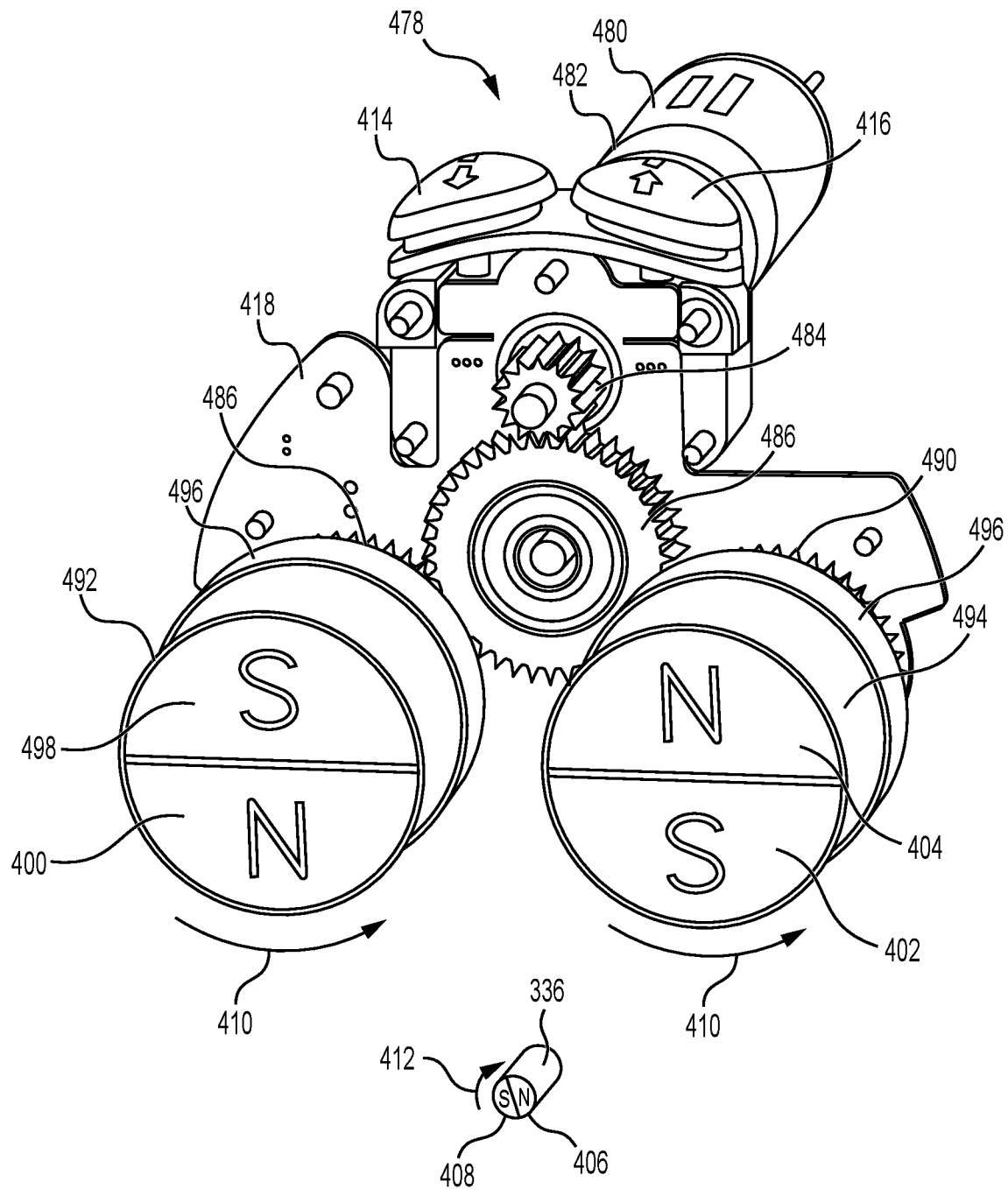
FIG. 11 illustrates the internal components of a handpiece of the external remote controller of FIG. 10.

FIG. 11 illustrates an internal assembly 478 of the magnetic handpiece 178 configured for applying a moving magnetic field to allow for non-invasive adjustment of the distraction device 110 by turning the magnet 338 within the distraction device 110. The magnet 338 of the distraction device 110 includes a north pole 406 and a south pole 408. A motor 480 with a gear box 482 outputs to a motor gear 484. The motor gear 484 engages and tunes a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 may be held within a respective magnet cup 496 (shown partially). An exemplary rotational speed may be 60 RPM or less. This speed range may be desired in order to limit the amount of current density included in the body tissue and fluids, to meet international guidelines or standards. As seen in FIG. 11, the south pole 498 of the first magnet 492 may be oriented the same as the north pole 404 of the second magnet 494, and likewise, the first magnet 492 has its north pole 400 oriented the same and the south pole 402 of the second magnet 494. As these two magnets 492, 494 turn synchronously together, they apply a complementary and additive moving magnetic field to the radially-poled, magnet 338. Magnets having multiple north poles (for example, two) and multiple south poles (for example, two) are also contemplated in each of the devices. Alternatively, a single magnet (e.g., a magnet with a larger diameter) may be used in place of the two magnets. As the two magnets 492, 494 turn in a first rotational direction 410 (e.g., counter-clockwise), the magnetic coupling causes the magnet 338 to turn in a second, opposite rotational direction 412 (e.g., clockwise). The rotational direction of the motor 480 may be controlled by buttons 414, 416. One or more circuit boards 418 contain control circuitry for both sensing rotation of the magnets 492, 494 and controlling the rotation of the magnets 492, 494.

FIGS. 7-9 and 12-13 illustrate the implantable adjustable system 100 incorporating a distraction device 110 and an External Remote Controller (ERC) 180 being used in a surgery and subsequent adjustment procedures to increase the length of a bone 502 in a residual limb 500. In some cases, the residual limb is a femur of an above-the-knee amputee. As seen in FIG. 7, the bone 502 may have an amputated end 504, and the residual limb 500 may have a stump surface 506. A prosthetic limb or prosthetic limb attachment which may be attached to a residual limb 500 may have problems fitting or functioning when attached to a residual limb 500 having insufficient bone 502 length. The medullary canal 514 of the bone 502 may be drilled or reamed to a diameter about equal or slightly larger than that of the distraction device 110 to be utilized. The bone 502 may be divided into a first bone portion 508 and a second bone portion 510 by creating an osteotomy 512. In FIG. 8, the distraction device 110 may be placed within the medullary canal 514 so that the one or more holes 210 are within the first portion 508 and the one or more holes 208 are within the second portion 510. During pre-operative planning, members of the surgical team will often assess both the condition and the coverage of soft tissues. The stump surface 506 may be modified, by stretching the skin or tissue, or by adding skin graft material, or performing plastic surgery, in order to create enough future available room for the bone 502 to increase in length inside the residual limb 500 in the area adjacent the stump surface 506. In addition, infection prevention measures are commonly performed. During pre-operative planning, several other factors are determined including: the amount of limb length discrepancy, the diameter of the medullary canal, the required length of distraction device 110 to be used, or the location of the planned osteotomy. In some cases, the distraction device may be implanted in an antegrade manner and in some cases in a retrograde manner. When implanted in an antegrade manner the distraction device 110 may be implanted via piriformis fossa entry. A retrograde approach may instead be chosen, for example, in patients with a severely abducted hip. In FIG. 9, bone screws 226, 224 are secured to the bone 502 through the holes 210, 208 in order to secure the distraction device 110 to the first and second bone portions 508, 510. The patient may be allowed to recover and at a later time, for example, about two to about ten days or about five days, the first distraction procedure may be performed. The ERC 180 may be placed on the residual limb 500 at a location adjacent the magnet 338, and is operated to distract the first bone portion 508 and the second bone portion 510 apart. The procedure may be repeated several times and may be performed by medical personnel, or the patient's family and friends, or even the patient themself. Exemplary distraction protocol may include distraction of about 0.50 mm to about 1.50 mm in longitudinal distraction per day. In some cases, it may include distraction of about 0.75 mm to about 1.25 mm in longitudinal distraction per day. In some cases, the distraction may be about 1.00 mm per day. This may be broken up into several distraction procedures per day, for example, about 0.33 mm, three times a day.

FIG. 12 illustrates the distraction device 110 in the bone 502 after the second distraction rod 206 has approximately been fully distracted in relation to the first distraction rod 204. Over the several weeks and/or months that the distraction procedures take place, a new bone growth section 516 of bone begins to form between the first portion 508 and the second portion 510. FIG. 13 illustrates the distraction device 110 in the bone 502 after the first distraction rod 204 has approximately been fully distracted in relation to the housing 202. After the desired final distraction length is reached, distraction procedures are discontinued, and the new bone growth section 516 may be allowed time to fully consolidate. The distraction device 110 can continue to provide stability to the bone 502 of the residual limb 500 while the bone 502 is allowed to consolidate and after the bone has consolidated. After consolidation, the distraction device 110 may then be removed from the patient, though in some cases, the distraction device 110 may be left in place within the bone 502.

Figure 14:
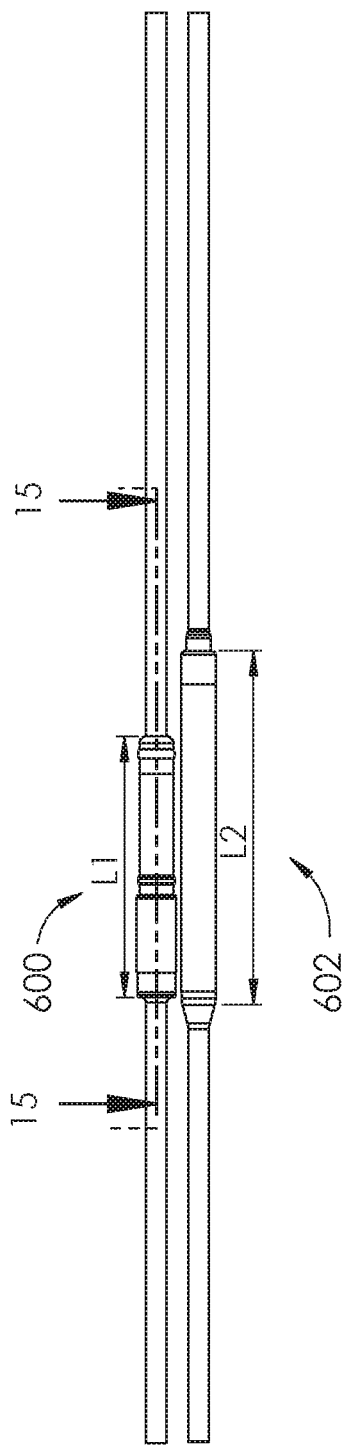
FIG. 14 illustrates a distraction device as disclosed herein placed next to a distraction device already in the prior art.
Figure 15:
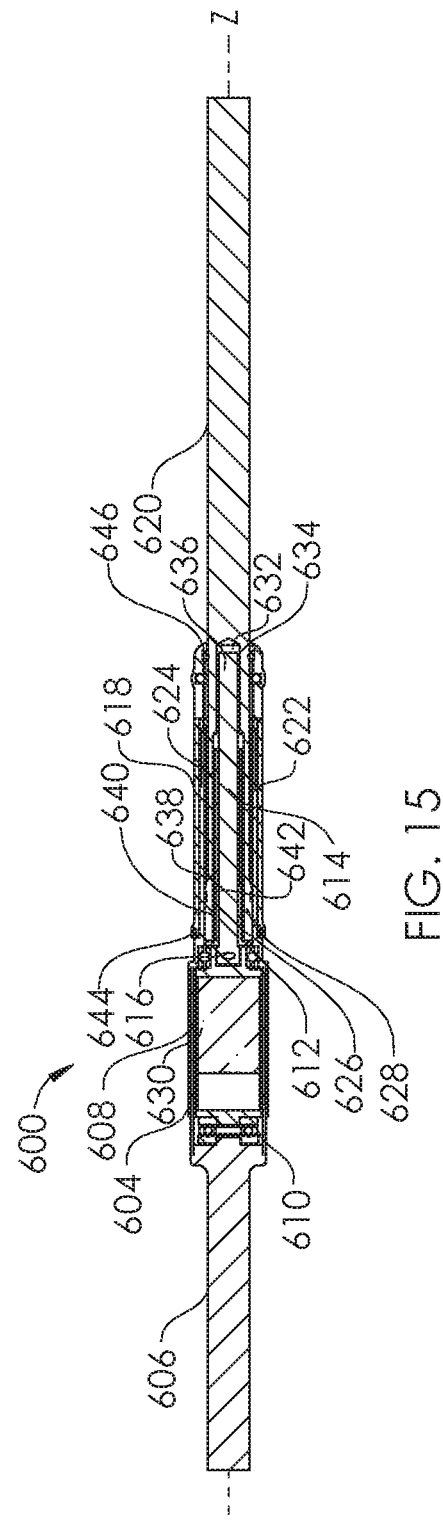
FIG. 15 illustrates a sectional view of the distraction device of FIG. 14 taken along line 15-15.

FIG. 14 illustrates one embodiment of a distraction device 600 placed next to a prior art distraction device 602. The distraction device 600 may be capable of distracting about 50 mm, as is the prior art distraction device 602, however the length $L_1$ of the housing portion of the distraction device 600 is over 25% percent shorter than the length $L_2$ of the housing portion of the prior art distraction device 602. The treatment of early onset scoliosis or adolescent idiopathic scoliosis is generally performed on small, thin patients having little space in their surgical sites to implant large device housings. Therefore, high efficiency adjustable distraction devices (total distraction length to housing length ratio) may allow more patients to be treated. Turning to FIG. 15, the distraction device 600 includes a housing 604 which may be connected to a rod 606 by welding Or other bonding methods. In some embodiments, the rod 606 and the housing 604 may be formed from the same monolithic material.

Within the housing 604, a driving element including a magnetic assembly 608 (containing a radially-poled magnet 630) may be held longitudinally stationary between a thrust bearing 610 and a radial bearing 612. Though gear modules may be incorporated, as in the embodiment of FIG. 1, in FIG. 15 the distraction device is depicted in an embodiment wherein the magnetic assembly 608 may be directly connected to a first lead screw 614 by a pin 616. In the distraction device 600 embodiment of FIG. 15, a first distraction rod 618 is telescopically carried on the outside of the housing 604, and is longitudinally displaceable along a longitudinal axis Z. A second distraction rod 620 may be telescopically carried within a cavity 622 within the housing 604, and is longitudinally displaceable along the longitudinal axis Z. The second distraction rod 620 has a cavity 632 which allows space for the first lead screw 614. A second lead screw 624 having an internal thread 626 at its proximal end 628 may be carried annularly between the first lead screw 614 and the second distraction rod 620. Rotation of the magnetic assembly 608 by a remotely-applied moving magnetic field causes the first lead screw 614 to rotate within the internal thread 626 of the second lead screw 624, thus causing the second lead screw 624 and the second distraction rod 620 to longitudinally displace in relation to the housing 604 and the first distraction rod 618. The distraction device 600 with the second distraction rod 620 fully displaced in relation to the first distraction rod 618 is illustrated in FIGS. 16-17. At this fully displaced condition, an abutment 634 at the distal end 636 of the first lead screw 614 abuts a ledge 638 at the proximal end 640 of the second lead screw 624. As the first lead screw 614 continues to turn, this causes the second lead screw 624 to turn in unison with the first lead screw 614, thus turning of the second lead screw 624 within an inner thread 642 within the cavity 632 of the second distraction rod 620. This causes the second distraction rod 620 to longitudinally displace further from the housing 604, dragging the first distraction rod 618 along with it. The distraction device 600 with the first distraction rod 618 fully displaced in relation to the housing 604 is illustrated in FIGS. 18-19. A first o-ring 644 held in a circumferential groove in the first distraction rod 618 forms a dynamic seal between the first distraction rod 618 and the housing 604. A second o-ring 646 held in a circumferential groove in the first distraction rod 618 forms a dynamic seal between the first distraction rod 618 and the second distraction rod 620. The distraction device 600 may be capable of retracting, by applying a moving magnetic field in an opposite direction, and causing the components to turn in opposite directions.

The distraction device 600 may comprise features to limit or stop rotation between the first distraction rod 618 and the housing 604, and/or between the second distraction rod 620 and the first distraction rod 618. For example, the longitudinal grooves, 216, 220 and protrusions 209, 211 of the embodiment of FIGS. 1-6 may be incorporated into the design of the distraction device 600, so that there may be substantially no rotation possible between the second distraction rod 620 and the housing 604. For example, if the second distraction rod 620 is rigidly coupled to a first vertebra (e.g., via a screw or hook) and the housing 604 (e.g., via rod 606) is coupled to a second vertebra (e.g., via a screw or hook), rotation may be substantially limited between the first vertebra and the second vertebra, so that no unwanted movement between them can occur. Furthermore, the abutments 289, 291, 293, 297 of the embodiment of FIGS. 1-6 may be incorporated into the design of the distraction device 600 in order to control the extent of lengthening of the first distraction rod 618 in relation to the housing 604, and/or the second distraction rod 620 in relation to the first distraction rod 618.

Figure 20:
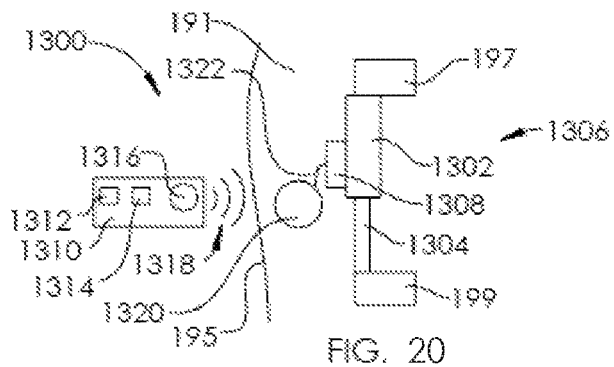
FIGS. 20-23 schematically illustrate various alternate sources of a driving element of a non-invasively adjustable spinal implant.

FIGS. 20-23 illustrate embodiments of alternate sources to the rotatable magnetic assembly as the driving element 242 of a non-invasively adjustable implant. FIG. 20 illustrates a non-invasively adjustable system 1300 comprising an implant 1306 having a first implant portion 1302 and a second implant portion 1304, the second implant portion 1304 non-invasively displaceable with relation to the first implant portion 1302. The first implant portion 1302 may be secured to a first bone portion 197 and the second implant portion 1304 may be secured to a second bone portion 199 within a patient 191. A motor 1308 may be operable to cause the first implant portion 1302 and the second implant portion 1304 to displace relative to one another. An external remote controller (ERC) 1310 has a control panel 1312 for input by an operator, a display 1314 and a transmitter 1316. The transmitter 1316 sends a control signal 1318 through the skin 195 of the patient 191 to an implanted receiver 1320. Implanted receiver 1320 communicates with the motor 1308 via a conductor 1322. The motor 1308 may be powered by an implantable battery, or may be powered or charged by inductive coupling.

Figure 21:
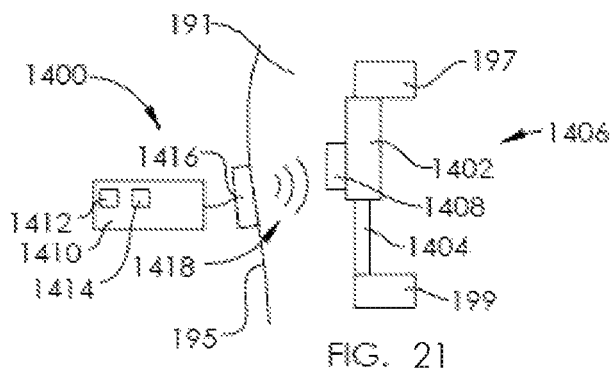

FIG. 21 illustrates a non-invasively adjustable system 1400 comprising an implant 1406 having a first implant portion 1402 and a second implant portion 1404, the second implant portion 1404 non-invasively displaceable with relation to the first implant portion 1402. The first implant portion 1402 may be secured to a first bone portion 197 and the second implant portion 1404 may be secured to a second bone portion 199 within a patient 191. An ultrasonic motor 1408 may be operable to cause the first implant portion 1402 and the second implant portion 1404 to displace relative to one another. An external remote controller (ERC) 1410 has a control panel 1412 for input by an operator, a display 1414 and an ultrasonic transducer 1416, which may be coupled to the skin 195 of the patient 191. The ultrasonic transducer 1416 produces ultrasonic waves 1418 which pass through the skin 195 of the patient 191 and operate the ultrasonic motor 1408.

Figure 22:
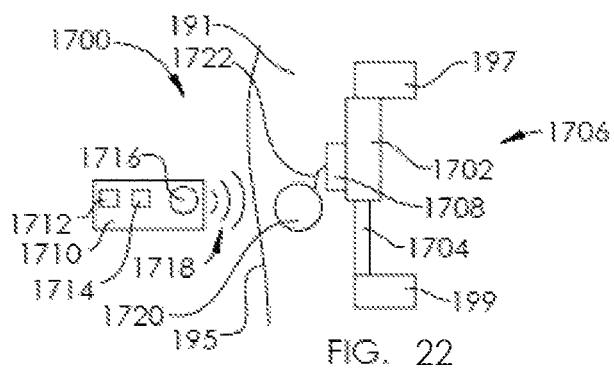

FIG. 22 illustrates a non-invasively adjustable system 1700 comprising an implant 1706 having a first implant portion 1702 and a second implant portion 1704, the second implant portion 1704 non-invasively displaceable with relation to the first implant portion 1702. The first implant portion 1702 may be secured to a first bone portion 197 and the second implant, portion 1704 may be secured to a second bone portion 199 within a patient 191. A shape memory actuator 1708 may be operable to cause the first implant portion 1702 and the second implant portion 1704 to displace relative to one another. An external remote controller (ERC) 1710 has a control panel 1712 for input by an operator, a display 1714 and a transmitter 1716. The transmitter 1716 sends a control signal 1718 through the skin 195 of the patient 191 to an implanted receiver 1720. Implanted receiver 1720 communicates with the shape memory actuator 1708 via a conductor 1722. The shape memory actuator 1708 may be powered by an implantable battery, or may be powered or charged by inductive coupling.

Figure 23:
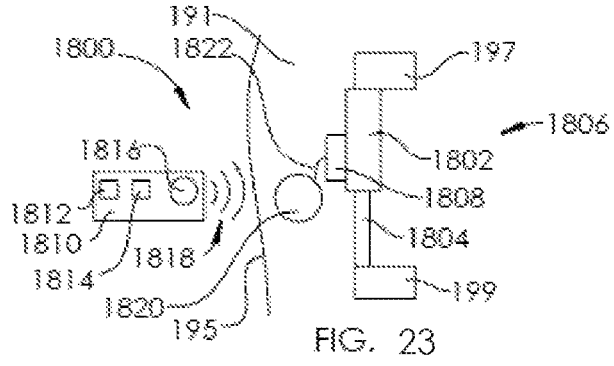

FIG. 23 illustrates a non-invasively adjustable system 1800 comprising an implant 1806 having a first implant portion 1802 and a second implant portion 1804, the second implant portion 1804 non-invasively displaceable with relation to the first implant portion 1802. The first implant portion 1802 may be secured to a first bone portion 197 and the second implant portion 1804 may be secured to a second bone portion 199 within a patient 191. A hydraulic pump 1808 may be operable to cause the first implant portion 1802 and the second implant portion 1804 to displace relative to one another. An external remote controller (ERC) 1810 has a control panel 1812 for input by an operator, a display 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable battery, or may be powered or charged by inductive coupling. The hydraulic pump 1808 may alternatively be replaced by a pneumatic pump.

Though not illustrated, another driving element 242 may include a magnetorestrictive element. A number of materials may be used to produce the components like the housing, first distraction rod, second distraction rod, first lead screw, and second lead screw, including but not limited to titanium, titanium alloys, titanium 6-4, cobalt-chromium alloys, and stainless steel.

Figure 24:
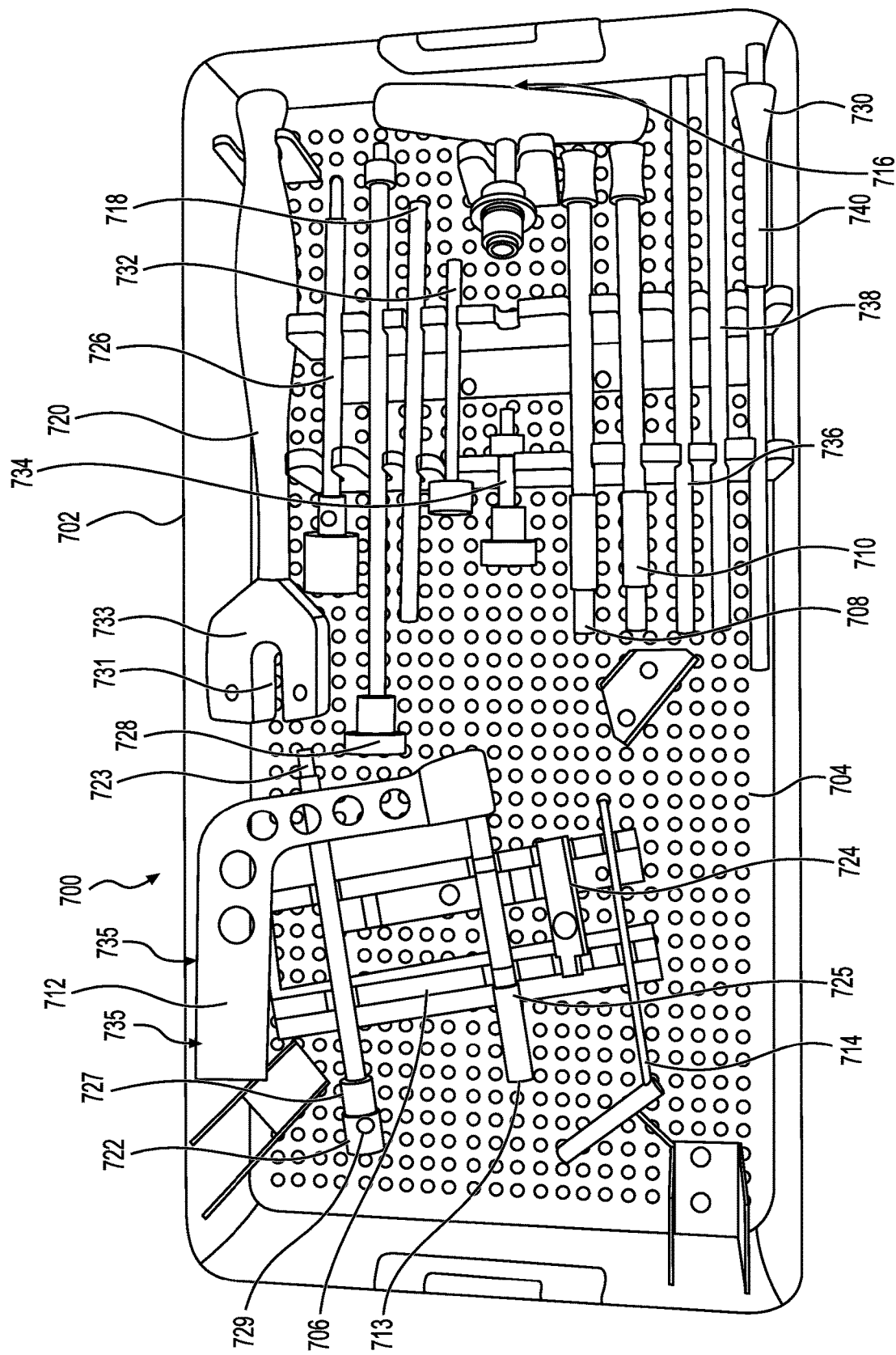
FIG. 24 illustrates a kit containing instruments for use with distraction devices according to embodiments described herein.

FIG. 24 illustrates a sterilizable kit 700 of instruments for use with embodiments of the distraction device described herein. A sterilizable tray 702 includes holes 704 which may allow gas or steam to enter the tray 702 when the tray 702 is covered by a cover (not shown). One or more dividers 706 may be constructed of a pliable material (such as silicone) and provide cavities, holes or slits therebetween for securing the one or more instruments. A drill bushing 708 and a guide tube 710 may be used for guiding one or more drills or reamers, for example, while drilling holes within the medullary canal of a bone. Prior to this, a hole may be made in the skin, soft tissue, and/or bone using a piercing rod 730. Vent holes may be made in the bone prior to reaming in order to avoid high intramedullary pressures which may cause fat embolism, or other complications. The medullary canal may in some cases be reamed to a slightly larger diameter than the diameter of the distraction device 110, for example 0.5 mm larger, or may be reamed 1 mm larger or 2 mm larger. A guide arm 712 may be connected at a distal end 713 of its guide tube 725 to a the housing 202 of the distraction device 110 of FIG. 6, for example an engagement portion 213 at the proximal end 221 of the housing 202. The engagement portion 213 may include a cavity, for example, a threaded cavity, and may be engageable via a distal end 723 of a locking rod 722. The locking rod 722 may be inserted through the guide tube 725 of the guide arm 712. The locking rod 722 may be tightened (or untightened) by turning a handle 727, or by placing a tommy bar 718 through a transverse hole 729 at or near the handle 727 of the locking rod 722. The drill bushing 708 and a guide tube 710 may be placed through transverse holes 735 in the guide arm, or a guide extension 724 may be secured to the end 737 of the guide arm 712. One or more additional transverse holes 735 may be within the guide extension for placement of the drill bushing 708 and a guide tube 710. During the manipulation of the distraction device 110 with the instruments, soft tissue of the patient may be protected with a soft tissue protector 714. Some or all of the cylindrical instrument components may be rotated with increased torque by attaching a T-handle 716. If the distraction device 110 and the guide arm 712 need to be removed, for example from a reamed medullary canal in the bone, a mallet 720 may be placed so that a slit 731 in the head 733 of the mallet 720 is around the guide tube 725 of the guide arm 712. The mallet 720 may be then caused to impact against the handle 727 of the guide arm 712 to aid in the removal of the distraction device 110 and guide arm 712. After implantation of the distraction device 110 and its securement to the bone by one or more bone screws, the guide arm 112 may be removed, by unscrewing the locking rod 722 from the engagement portion 213 of the distraction device 110.

If the distraction device 110 is to be removed from the bone (for example after the bone has been lengthened and allowed to consolidate), after the bone screws are removed, an extractor 726 may be attached to the engagement portion 213 of the distraction device 110 and the distraction device may be pulled out of the medullary canal by hand, or may be hammered out using the mallet 731. The distal end of the extractor 726 may have a male or female thread that can be engaged with the proximal end 221 of the housing 202 of the distraction device 110. An additional removal rod 728 may be used. Further instruments that may be used include a locking key 732, a short impactor 734, a hexagon headed river 736 and a locking driver 738. Bone screws 740 may be secured with a screw capture rod 740. Other instruments and uses of instruments are described in U.S. Pat. No. 8,449,543, which is incorporated herein by reference in its entirety.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A system comprising:
   an adjustable implant including:
      an actuator positioned within a housing;
      a drive element coupled to the actuator and configured to rotate upon actuation of the actuator;
      a first moveable member configured to move in relation to the drive element and the housing in response to rotation of the drive element; and
      a second moveable member telescopically displaceable from within a cavity of the first moveable member in response to rotation of the drive element,
      wherein at least a portion of the first moveable member at a proximal end thereof surrounds a portion of the housing such that, upon actuation of the actuator, the first moveable member translates longitudinally along an exterior of the housing; and
an adjustment device configured to cause actuation of the actuator, the adjustment device positioned external to the adjustable implant.

2. The system of claim 1, wherein the drive element includes an external thread.

3. The system of claim 1, wherein the drive element includes a lead screw.

4. The system of claim 1, wherein the actuator includes a magnet, a motor, a shape memory actuator, an ultrasonic motor, or a hydraulic pump.

5. The system of claim 4, wherein the actuator includes the motor.

6. The system of claim 4, wherein the actuator includes the shape memory actuator.

7. The system of claim 4, wherein the actuator includes the magnet and the magnet includes a radially-poled permanent magnet.

8. The system of claim 1, wherein the second moveable member is configured to move in a first direction about the housing such that a length of the adjustable implant increases and in a second, opposite direction about the housing such that the length of the adjustable implant decreases.

9. The system of claim 1, wherein the second moveable member comprises a rod configured to move relative to the housing upon actuation of the actuator, and wherein the rod is at least partially disposed within the first moveable member.

10. A system comprising:
an adjustable implant:
a first sleeve configured to be coupled to a first bone portion;
a second sleeve configured to move in relation to the first sleeve to change a length of the adjustable implant;
an actuator; and
a drive element coupled to the actuator and configured to rotate upon actuation of the actuator thereby causing the second sleeve to move in relation to the first sleeve,
wherein the second sleeve comprises a first moveable member and a second moveable member telescopically displaceable from within a cavity of the first moveable member in response to rotation of the drive element, and wherein the second sleeve translates longitudinally along an exterior of the first sleeve upon actuation of the actuator; and
an adjustment device configured to cause actuation of the actuator, the adjustment device positioned external to the adjustable implant.

11. The system of claim 10, wherein the drive element includes an external thread.

12. The system of claim 10, wherein the drive element includes a lead screw.

13. The adjustable implant of claim 10, wherein the actuator includes a magnet, a motor, a shape memory actuator, an ultrasonic motor, or a hydraulic pump.

14. The system of claim 13, wherein the actuator includes the motor.

15. The system of claim 13, wherein the actuator includes the shape memory actuator.

16. The system of claim 13, wherein the actuator includes the magnet and the magnet includes a radially-poled permanent magnet.

17. The system of claim 10, wherein the second moveable member is configured to move in a first direction about the housing such that a length of the adjustable implant increases, and in a second, opposite direction about the housing such that the length of the adjustable implant decreases.

18. The system of claim 10, further comprising:
a rod configured to move relative to the housing upon actuation of the actuator, wherein the rod is at least partially disposed within the first moveable member.

19. A distraction and retraction system comprising:
a distraction and retraction device including:
a housing having an actuator positioned therein;
a drive element coupled to the actuator and configured to rotate in response to actuation of the actuator;
a first rod configured to move in relation to the drive element and the housing in response to rotation of the drive element; and
a second rod telescopically displaceable from within a cavity of the first rod in response to rotation of the drive element,
wherein the first rod is configured to translate longitudinally along an exterior of the housing upon actuation of the actuator, wherein actuation of the actuator in one direction causes the first rod to translate along the exterior of the housing such that an overall length of the device increases, and wherein actuation of the actuator in another, opposite direction causes the first rod to translate along the exterior of the housing such that an overall length of the device decreases; and
an adjustment device configured to cause actuation of the actuator, the adjustment device positioned external to the distraction and retraction device.

20. The system of claim 1, wherein the second moveable member is telescopically displaceable from within the cavity at a distal end of the first moveable member in response to rotation of the drive element, and wherein at least the portion of the first moveable member at the proximal end thereof surrounds the portion of the housing.

* * * * *